(12) United States Patent
Majeed et al.

(10) Patent No.: US 9,220,703 B2
(45) Date of Patent: Dec. 29, 2015

(54) COMPOSITION AND METHOD FOR THE PROTECTION OF ARTICULAR CARTILAGE

(71) Applicants: Muhammed Majeed, Edison, NJ (US); Kalyanam Nagabhushanam, East Windsor, NJ (US); Sarang Bani, Bangalore (IN); Anjali Pandey, Bangalore (IN)

(72) Inventors: Muhammed Majeed, Edison, NJ (US); Kalyanam Nagabhushanam, East Windsor, NJ (US); Sarang Bani, Bangalore (IN); Anjali Pandey, Bangalore (IN)

( * ) Notice: Subject to any disclaimer, the term of this patent is extended or adjusted under 35 U.S.C. 154(b) by 0 days.

(21) Appl. No.: 14/152,097

(22) Filed: Jan. 10, 2014

(65) Prior Publication Data

US 2015/0196524 A1    Jul. 16, 2015

(51) Int. Cl.
*A61K 31/235*    (2006.01)

(52) U.S. Cl.
CPC .................................. *A61K 31/235* (2013.01)

(58) Field of Classification Search
None
See application file for complete search history.

(56) References Cited

U.S. PATENT DOCUMENTS

2013/0012579 A1*  1/2013  Majeed et al. ................ 514/543

OTHER PUBLICATIONS

Joosten, IL-1αβ Blockade Prevents Cartilage and Bone Destruction in Murine Type II Collagen-Induced Arthritis, Whereas TNF-α Blockade Only Ameliorates Joint Inflammation, Journal of Immunology, 1999, pp. 5049-5055.*

* cited by examiner

*Primary Examiner* — San-Ming Hui
*Assistant Examiner* — Andrew Lee

(57) ABSTRACT

The novel therapeutic potential of Calebin A and compositions thereof to prevent pathological damage to mammalian articular cartilage is disclosed.

3 Claims, 2 Drawing Sheets x400 x400

COMPOSITION AND METHOD FOR THE PROTECTION OF ARTICULAR CARTILAGE

BACKGROUND OF THE INVENTION

1. Field of the Invention

The present invention in general pertains to protective compositions and methods thereof for articular cartilage. Specifically, the present invention pertains to the potential of Calebin A to prevent pathological damage to articular cartilage.

2. Description of Prior Art

Articular cartilage is a specialized connective tissue that covers the articular surfaces of bones forming a synovial joint. Articular cartilage endows the synovial joints the ability to provide low friction and relatively pain free motion. Articular cartilage structures and functions are prone to damage following trauma (fall or accident), wear and tear and underlying pathological disease conditions. Articular cartilage tissue usually does not regenerate (the process of self repair) after injury or disease leading to loss of tissue and formation of a defect. Reasons attributed to such non-regeneration include (i) Fewer cellular components; (ii) poor metabolism and (iii) the restricted capacity of innate chondrocytes to divide and migrate in the tissue on account of dense matrix fibers. Thus, active principles that are capable of protecting articular cartilage from damage due to trauma and disease constitute important technological areas that offer considerable scope to improve the quality of life of individuals who are prone to such trauma.

It is the principle of the present invention to disclose the potential of Calebin A and compositions thereof to prevent pathological damage to mammalian articular cartilage.

The present invention fulfills the aforesaid objective and provides further related advantages.

SUMMARY OF THE INVENTION

The present invention relates to the potential of Calebin A and compositions thereof to prevent pathological damage to mammalian articular cartilage.

The present invention provides the following advantage.

1. Disclosure of the novel therapeutic potential of Calebin A and compositions thereof to prevent pathological damage to mammalian articular cartilage.

Other features and advantages of the present invention will become apparent from the following more detailed description, taken in conjunction with the accompanying images, which illustrate, by way of example, the principle of the invention.

Figure 1:
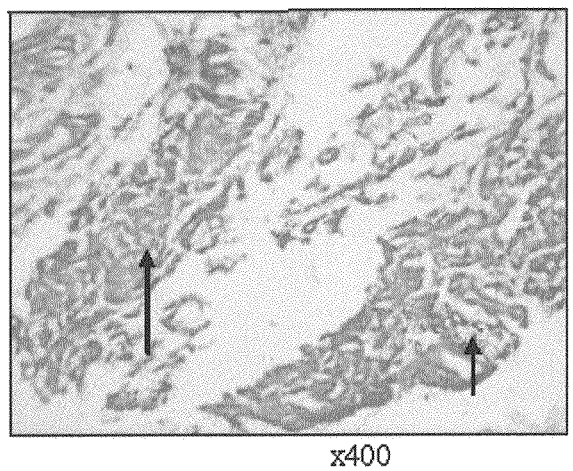
FIG. 1 shows the histopathology of the rat paw tissue section of arthritic control group.
Figure 2:
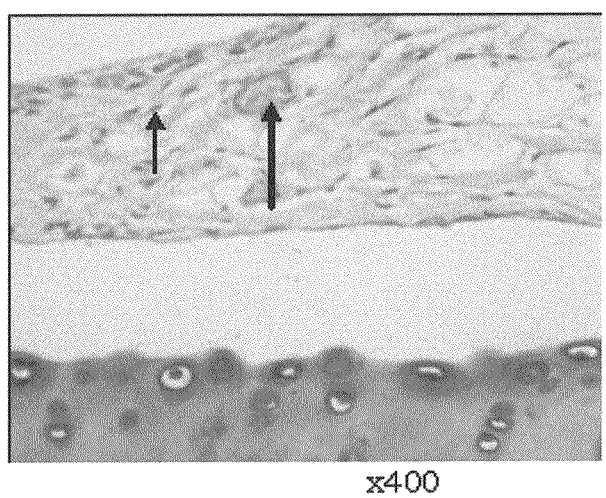
FIG. 2 shows the histopathology of the rat paw tissue section of the group treated with Calebin A (10 mg/kg).
Figure 3:
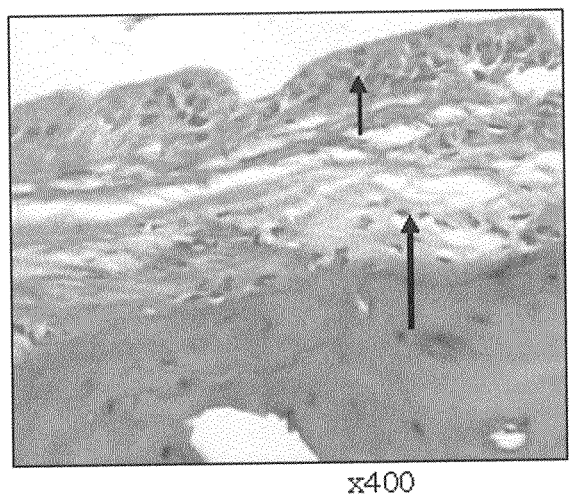
FIG. 3 shows the histopathology of the rat paw tissue section of the group treated with Calebin A (20 mg/kg).

DETAILED DESCRIPTION OF THE MOST PREFERRED EMBODIMENT (FIGS. 1, 2 and 3)

In the most preferred embodiment, the present invention relates to a method of using Calebin A in effective amounts to protect mammalian articular cartilage from pathological damage, said method comprising the step of administering effective dose of Calebin A to mammals in need of said protection.

In another preferred embodiment, the present invention relates to the method of protecting mammalian articular cartilage from pathological damage, said method comprising the step of administering effective dose of Calebin A to mammals in need of said protection.

The novel therapeutic potential of Calebin A and compositions thereof to prevent pathological damage to mammalian articular cartilage is clearly enunciated in the illustrative examples discussed herein below.

ILLUSTRATIVE EXAMPLE 1

Pathological damage: Adjuvant induced arthritis in animal models

Animals used: Albino Wistar rats of either sex
Weight of the animals: 140-180 grams
Number of animals/group: 5
Methodology: Chronic arthritis was induced in rats by the injection of 0.05 mL of (0.5% w/v) suspension of killed *Mycobacterium tuberculosis*, homogenized in liquid paraffin in the left hind foot.

TABLE A

Scheme of work for screening of Calebin A in *Mycobacterium tuberculosis* (adjuvant) induced arthritis in mammals

| Animal Group | Test compound | Treatment |
|---|---|---|
| Group 1 | Naïve control | Vehicle |
| Group 2 | Arthritic control | Vehicle + 0.5% w/v adjuvant |
| Group 3 | Acetyl salicylic acid (ASA) 100 mg/kg. (per oral) | ASA + 0.5% w/v adjuvant |
| | Calebin A | |
| Group 4 | 2.5 mg/kg (per oral administration) | Test compound + 0.5% w/v adjuvant |
| Group 5 | 5 mg/kg (per oral administration) | Test compound + 0.5% w/v adjuvant |
| Group 6 | 10 mg/kg (per oral administration) | Test compound + 0.5% w/v adjuvant |
| Group 7 | 20 mg/kg (per oral administration) | Test compound + 0.5% w/v adjuvant |

Histopathology:

Right ankle joints of the animals in the control and treated groups were separated from the hind paw, weighed and immersed in 10% buffered formalin for 24 hours, followed by decalcification in 10% EDTA. The joints were then dehydrated, processed and paraffin (56 C-58 C) blocks were prepared, stained (hematoxylin and eosin) and examined under the compound microscope (Patel P, Patel D, Patel N. Experimental investigation of anti-rheumatoid activity of *Pleurotus sajorcaju* in adjuvant-induced arthritic rats. Chinese Journal of Natural Medicines, 2012; 10 (4): 0269-0274.

Histopathology Results:

The rat paw tissue of the control arthritic group showed (FIG. 1) focally damaged articular cartilage with synovial tissue (Arrows). The articular cartilage and synovial tissue were replaced by abundant eosinophilic caeseous necrosis with scattered epitheloid cells and there were few poorly formed ill-defined granulomas.

The rat paw tissue of the group treated with Calebin A (10 mg/kg) [FIG. 2] showed intact articular cartilage with synovial tissue in the joint. The synovial tissue consisted of congested vascular spaces (Long-Arrows), scattered lymphocytes (Short-Arrow) and intact synovial lining. No granulomas were seen.

The rat paw tissue of the group treated with Calebin A (20 mg/kg) [FIG. 3] showed intact articular cartilage with synovial tissue in the joint. The synovial tissue consisted of mild synovial epithelial hyperplasia (Short-Arrow), scattered lymphocytes (Long-Arrow) and intact vascular spaces. No granulomas were seen.

The histopathological studies of arthritic rats shows dose dependant protection of articular cartilage with Calebin A.

While the invention has been described with reference to a preferred embodiment, it is to be clearly understood by those skilled in the art that the invention is not limited thereto. Rather, the scope of the invention is to be interpreted only in conjunction with the appended claims.

We claim:

1. A method of using Calebin A in effective amounts to protect mammalian articular cartilage from necrotic damage following microbial infection, said method comprising the step of administering orally, effective dose of Calebin A based on body weight to mammals affected by said microbial infection and are in need of articular cartilage protection.

2. A method of protecting mammalian articular cartilage from necrotic damage following microbial infection, said method comprising the step of administering orally, effective dose of Calebin A based on body weight to mammals affected by said microbial infection and are in need of said articular cartilage protection.

3. The methods according to claims 1 and 2 wherein the microbial infection is caused by *Mycobacterium tuberculosis* and antigens thereof.

* * * * *